United States Patent [19]

Clark et al.

[11] Patent Number: 5,356,631

[45] Date of Patent: * Oct. 18, 1994

[54] PHARMACEUTICAL COMPOSITION

[75] Inventors: Andrew R. Clark, Loughborough; Anne M. Hollingworth, Shepshed, both of England

[73] Assignee: Fisons plc, Ipswich, England

[*] Notice: The portion of the term of this patent subsequent to Mar. 30, 2010 has been disclaimed.

[21] Appl. No.: 10,480

[22] Filed: Jan. 28, 1993

Related U.S. Application Data

[60] Division of Ser. No. 835,014, Feb. 12, 1992, Pat. No. 5,198,221, which is a continuation of Ser. No. 522,998, May 14, 1990, abandoned.

[30] Foreign Application Priority Data

May 17, 1989 [GB] United Kingdom ............... 89/11259

[51] Int. Cl.$^5$ ................................................. A23K 1/18
[52] U.S. Cl. .................................... 424/438; 424/439
[58] Field of Search ........................................ 424/434

*Primary Examiner*—John Kight, III
*Assistant Examiner*—William E. BenstIon, Jr.
*Attorney, Agent, or Firm*—Marshall, O'Toole, Gerstein, Murray & Borun

[57] ABSTRACT

Particulate nedocromil sodium with a mass median diameter of from 5 to 10 μm is useful as a medicament for inhalation.

The particulate nedocromil sodium of the invention is particularly advantageous in that its dispersion, i.e. the proportion of particles which are capable of penetrating deep into the lung, is substantially greater than the dispersion of conventional powders having smaller mass median diameters.

8 Claims, No Drawings

PHARMACEUTICAL COMPOSITION

This is a division of application Ser. No. 07/835,014, filed Feb. 12, 1992 now U.S. Pat. No. 5,198,221 which is in turn a Continuation of Ser. No. 07/522,998, filed on May 14, 1990, now abandoned.

This invention relates to a novel powder form of the known medicament nedocromil sodium, and to pharmaceutical formulations comprising that powder form.

Nedocromil sodium, the disodium salt of 9-ethyl-6,9-dihydro-4,6-dioxo-10-propyl-4H-pyrano[3,2-g] quinoline-2,8-dicarboxylic acid, is known, for example from British Patent Application No 2157291, to be of use in the treatment of reversible obstructive airways disease when administered to the lung in finely divided solid form.

An important parameter affecting the efficacy of powder formulations for inhalation is the 'dispersion' i.e. the proportion of the inhaled powder cloud which is fine enough to penetrate deep into the lung. For administration in this form, it has previously generally been considered that the dispersion of inhalation medicaments improves as the average particle size is reduced. European Patent No 0072046, for example, states that the smaller the mass median diameter, the higher will be the dispersion. The above mentioned British Patent Application No 2157291 is consistent with this, since it expresses a preference for nedocromil sodium with a mass median diameter of less than 4 $\mu$m, and particularly less than 3 $\mu$m.

We have now surprisingly found that nedocromil sodium powders with average particle sizes considerably greater than those previously considered desirable actually give better dispersion than such finer powders.

According to the invention there is provided particulate nedocromil sodium with a mass median diameter of from 5 to 10 $\mu$m.

The particulate nedocromil sodium of the invention is advantageous in that its dispersion, i.e. the proportion of particles which are capable of penetrating deep into the lung, is substantially greater than the dispersion of conventional powders having smaller mass median diameters. This increases the effective dose administered and may enable the use of lower total dosages. In addition, the material may exhibit other advantageous properties, e.g. improved emptying from the device used for administration and/or greater efficacy when administered at low or moderate flow rates.

The mass median diameter, as is known by those skilled in the art, is defined such that 50% by mass of the particulate material is in the form of particles having a smaller diameter. Throughout this specification, the term is used to indicate the mass median diameter as determined by laser diffraction light scattering techniques. Similarly, other particle sizes referred to are as measured by these techniques. The use of other methods of particle sizing may give results which differ somewhat from those obtained by the light scattering technique.

We prefer the mass median diameter of the particulate nedocromil sodium according to the invention to be less than 9 μm.

Thus, we prefer the mass median diameter of the particulate nedocromil sodium according to the invention to be in the range 5 to 9 μm.

The particle size distribution of the particulate nedocromil sodium may also be characterised in terms of the mass fractions above or below certain limits. We prefer the mass fraction of material which is present as particles with a diameter greater than 10 μm to be less than 40%. The mass fraction of the medicament which is present as particles which have a diameter of less than 3 μm is preferably more than 5%, and more preferably more than 10%.

The particle size distribution may also be characterised by the geometric standard deviation $SD_{geo}$. This quantity may be obtained from a logarithmic plot of the cumulative percentage less than a stated size against the logarithm of the size. Such a plot is generally a straight line and $SD_{geo}$ can be obtained from the relation $$SD_{geo} = 84.13\%\ \text{size}/50\%\ \text{size} = 50\%\ \text{size}/15.87\%\ \text{size}$$

(see Eugene L Parrott in The Theory and Practice of Industrial Pharmacy, Chapter 2, page 21, published by Lea & Febiger, Philadelphia) in which 'n % size' is the diameter for which n % of the material is smaller than the stated size. In this specification, geometric standard deviations are quoted on a mass basis, though in practice geometric standard deviations for weight and number distributions are practically identical.

We prefer the geometric standard deviation of the particle size distribution to be in the range 1.5 to 3.0, more preferably 2.0 to 2.7.

According to a particularly preferred aspect of the invention there is provided particulate nedocromil sodium having a mass median diameter of from 5 to 10 μm and a geometric standard deviation of from 1.5 to 3.0.

As mentioned above, particle sizes quoted in this specification are as determined by laser diffraction light scattering techniques. Other suitable methods of particle size determination may be used. In general, such methods will be well known to those skilled in the art and include microscopy and sedimentation. Sieving methods, which are also widely used for particle size determination, are generally not suitable in the present case due to the small size of the particles. More details of methods of particle size determination may be obtained from, for example, the article by Parrott referred to above and the references therein.

The particulate nedocromil sodium according to the invention may be prepared by conventional methods used for the preparation of finely divided material, e.g. milling and micronisation. Various types of mill may be used but we have found the use of a hammer mill to be particularly convenient. The hammer mill is well known and is an impact mill using a high speed rotor to which a number of swinging hammers are fixed. The material is fed at the top or centre, thrown out centrifugally, and ground by impact of the hammers or against plates around the periphery of the casting. The clearance between the housing and the hammers contributes to the size reduction. The material is retained until it is small enough to fall through the screen that forms the lower portion of the casing. Particles fine enough to pass through the screen are discharged almost as fast as they are formed.

The optimum operating conditions for the hammer mill will vary depending inter alia on the particle size of the material fed to the mill, the particular model of mill used etc. Parameters which may be varied include the rotational speed of the rotor and the form (thickness and mesh size) of screen employed.

The use of a hammer mill is preferred because it is particularly suitable for the production of material with the appropriate particle size and is generally simple to install and operate. The rotational speed and screen can be rapidly changed and particulate material with a relatively narrow particle size distribution is obtained.

The particulate nedocromil sodium according to the invention will generally be manufactured in a form suitable for direct administration to a patient. For example, the material may be formulated as the active ingredient in a composition containing the particulate nedocromil sodium in admixture with a solid pharmaceutically acceptable carrier having an effective particle size of from 30 to 120 $\mu m$.

The term 'effective particle size' is used to denote the apparent particle size of a body without distinction as to the number of individual particles which go to make up that body i.e. no distinction is made between a single particle of given size and an agglomerate of the same size which is composed of finer individual particles.

The solid pharmaceutically acceptable carrier in the composition will generally be a non-toxic material chemically inert to nedocromil sodium but may, if so desired, also comprise larger particles of nedocromil sodium. Examples of carriers which may be used in the composition include a dextran, mannitol and, preferably, lactose. A particularly preferred carrier is crystalline lactose.

The particles of carrier preferably have a mass median diameter of from about 30 to 150 $\mu m$. The mass median diameter is preferably less than 100 $\mu m$ and more preferably less than 80 $\mu m$. It is particularly preferred that the mass median diameter of the carrier particles be in the range 30 to 80 $\mu m$, e.g. about 50 to 60 $\mu m$.

According to a further, preferred aspect of the invention there is provided a pharmaceutical composition comprising particles of nedocromil sodium having a mass median diameter of from 5 to 10 $\mu m$, in admixture with a solid pharmaceutically acceptable carrier having a mass median diameter of from 30 to 80 $\mu m$, the proportion by weight of nedocromil sodium to carrier being in the range 1:4 to 4:1.

The particulate carrier may be prepared by grinding the carrier and subsequently separating out the desired fraction by conventional methods, e.g. by air classification and sieving.

The composition may be prepared by mixing the ingredients together in a mixer, e.g. a planetary or other stirred mixer. The invention thus also provides a method for preparing a composition of the invention which comprises mixing together particulate nedocromil sodium according to the invention and the coarse carrier, after comminution and particle size classification of the ingredients if this is necessary.

The particulate nedocromil sodium may also be formulated as a so-called 'pelletised' composition, i.e. as soft pellets of diameter greater than 30 $\mu m$, each pellet comprising a plurality of individual particles loosely held together such that upon inhalation the pellets disintegrate to the constituent particles.

The compositions according to the invention may be put up in gelatine, plastics or other capsules.

The amount of composition contained in the capsule will, of course, to some extent depend on the desired dosage, but will generally be from about 10 to 50 $\mu mg$, e.g. 20 mg. The proportion of nedocromil sodium in the composition will typically be from about 25 to 50%.

There is also provided therefore, as a further feature of the invention, a dosage unit comprising a capsule containing from 10 to 50 mg of a pharmaceutical composition comprising particles of nedocromil sodium having a mass median diameter of from 5 to 10 $\mu m$ in admixture with coarser particles of a solid pharmaceutically acceptable carrier.

A method of preparation of nedocromil sodium is described in Canadian Patent No 1112644. A form of nedocromil sodium which is particularly well suited to grinding and a method of preparing such that form is described in British Patent Application No 2157291.

The present invention will now be illustrated by the following Examples.

EXAMPLE 1

Preparation of Nedocromil Sodium according to the Invention

Recrystallised nedocromil sodium, prepared by a method similar to that of Example 2 of British Patent Application No 2157291, was passed through a hammer mill (Model TBEP manufactured by Apex Construction Ltd, Dartford, UK) operating at a rotational speed of 3450 rpm with a screen size of 2 mm and the milled product collected in kegs with double polyethylene lining.

EXAMPLE 2

Particle size determination

The particle size distribution of milled nedocromil sodium prepared as described in Example 1 was determined using a Malvern 2600 Series Laser Diffraction Particle Sizer (Malvern Instruments plc, Malvern, UK) fitted with a 63 mm lens and operating in p-i-l (particles in liquid) mode, as follows:

With the sample cell filled with filtered propan-2-ol, the optics were aligned and the diffracted light measured with no sample present to establish the baseline. A small test tube was rinsed with propan-2-ol, then half filled with filtered propan-2-ol and a small sample of the particulate nedocromil sodium was added. The tube was manually agitated to facilitate wetting and placed in an ultrasonic bath for two minutes to disperse the solid particles.

Suspended particles from the testtube were added to the sample cell from the test tube using a Pasteur pipette untile the optimum sample concentration was reached, whereupon the measurement was made.

EXAMPLE 3

Comparison of Capsule Emptying and Dispersion for Two Formulations of Nedocromil Sodium Method Number 2 hard gelatine capsules were filled with 20 mg of 1:1 nedocromil sodium: lactose blends in which the nedocromil sodium had a mass median diameter (MMD) of approximately 2 $\mu m$ and 8 $\mu m$.

The capsules were loaded into the inhaler sold under the registered trademark SPINHALER (Fisons plc). The device was discharged in a multi-stage impinger (described in, for example, Bell J. H., Hartley P. S., & Cox P. S. G., J Pharm Sci 60, 10 (1971)) at a flow rate of 60 l/min or 120 l/min and the quantity of material retained in the device and the quantity of respirable material (particles of diameter less than 7.5 $\mu m$ at 60 l/min and 5.0 $\mu m$ at 120 l/min) were measured.

Results

| Flow Rate | quantity of nedocromil sodium/mg | | | |
|---|---|---|---|---|
| | 60 l/min | | 120 l/min | |
| MMD (μm) | 2 | 8 | 2 | 8 |
| Device retention | 3.75 | 2.40 | 4.56 | 2.11 |
| Fine particle dose | 0.46 | 1.86 | 2.66 | 3.99 |

EXAMPLE 4

Pharmaceutical Compositions Containing Nedocromil Sodium

| | % w/w |
|---|---|
| a) Nedocromil sodium | 50 |
| Crystalline lactose | 50 |
| b) Nedocromil sodium | 37.5 |
| Crystalline lactose | 62.5 |
| c) Nedocromil sodium | 25 |
| Crystalline lactose | 75 |

In each case the nedocromil sodium has a mass median diameter of approximately 8 μm. The crystalline lactose is classified and has a mass median diameter of approximately 55 μm. The compositions are prepared by mixing the ingredients in a planetary mixer.

We claim:

1. A pharmaceutical inhalation composition comprising soft pellets of nedocromil sodium of diameter greater than 30 μm, each pellet comprising a plurality of individual particles loosely held together such that upon inhalation the pellets disintegrate to the constituent particles, the mass median diameter of the constituent particles being from 5 to 10 μm with a particle size geometric standard deviation of from 1.5 to 3.0.

2. A pharmaceutical composition according to claim 1, wherein the mass median diameter of the constituent particles is less than 9 μm.

3. A pharmaceutical composition according to claim 1, wherein the mass fraction of material which is present as constituent particles with a diameter greater than 10 μm is less than 40%.

4. A pharmaceutical composition according to claim 1, wherein the mass fraction of material which is present as constituent particles which have a diameter of less than 3 μm is more than 5%.

5. A pharmaceutical composition according to claim 1, wherein the mass fraction of material which is present as constituent particles which have a diameter of less than 3 μm is more than 10%.

6. A pharmaceutical composition according to claim 1, wherein the geometric standard deviation of the particle size distribution is from 2.0 to 2.7.

7. A capsule containing from 10 to 50 mg of a pharmaceutical composition according to claim 1.

8. A method of treatment of reversible obstructive airways disease, which method comprises administration to a patient suffering from or susceptible to such a condition of a therapeutically effective quantity of a pharmaceutical composition according to claim 1.

* * * * *

UNITED STATES PATENT AND TRADEMARK OFFICE
CERTIFICATE OF CORRECTION

PATENT NO. : 5,356,631

DATED : October 18, 1994

INVENTOR(S) : ANDREW R. CLARK ET AL.

It is certified that error appears in the above-identified patent and that said Letters Patent is hereby corrected as shown below:

Column 3, third line from bottom, "50 μmg" should be --50 mg--

Signed and Sealed this

Twenty-fourth Day of January, 1995

Attest:

BRUCE LEHMAN

Attesting Officer     *Commissioner of Patents and Trademarks*